(12) United States Patent
Guimont et al.

US010362850B2

(10) Patent No.: US 10,362,850 B2
(45) Date of Patent: Jul. 30, 2019

(54) DYE-FREE NAIL VARNISH COMPOSITIONS AND METHODS THEREOF

(71) Applicant: L'Oréal, Paris (FR)

(72) Inventors: Aline Guimont, South Orange, NJ (US); Marta Wolska-Brys, Jersey City, NJ (US); Chunhua Li, Hillsborough, NJ (US); Rong Dong, Highland Park, NJ (US)

(73) Assignee: L'Oréal, Paris (FR)

( * ) Notice: Subject to any disclaimer, the term of this patent is extended or adjusted under 35 U.S.C. 154(b) by 0 days.

(21) Appl. No.: 15/403,051

(22) Filed: Jan. 10, 2017

(65) Prior Publication Data

US 2018/0192758 A1 Jul. 12, 2018

(51) Int. Cl.
| | |
|---|---|
| *A45D 29/00* | (2006.01) |
| *A61Q 3/02* | (2006.01) |
| *A61K 8/02* | (2006.01) |
| *A61K 8/90* | (2006.01) |
| *A61K 8/895* | (2006.01) |

(52) U.S. Cl.
CPC ............ *A45D 29/00* (2013.01); *A61K 8/0241* (2013.01); *A61K 8/895* (2013.01); *A61K 8/90* (2013.01); *A61Q 3/02* (2013.01); *A45D 2029/005* (2013.01); *A61K 2800/30* (2013.01); *A61K 2800/437* (2013.01); *A61K 2800/81* (2013.01); *A61K 2800/88* (2013.01)

(58) Field of Classification Search
None
See application file for complete search history.

(56) References Cited

U.S. PATENT DOCUMENTS

| 5,985,951 | A | 11/1999 | Cook | |
|---|---|---|---|---|
| 8,399,537 | B2 | 3/2013 | Conger et al. | |
| 8,901,199 | B2 | 12/2014 | Vu et al. | |
| 2006/0002875 | A1* | 1/2006 | Winkler | A61K 8/11 424/63 |
| 2008/0253980 | A1* | 10/2008 | Weber | A61K 8/02 424/61 |
| 2010/0040741 | A1 | 2/2010 | Butler | |
| 2011/0265809 | A1 | 11/2011 | Jeon | |
| 2014/0323323 | A1 | 10/2014 | Cunningham et al. | |
| 2015/0158911 | A1 | 1/2015 | Parker et al. | |
| 2015/0329604 | A1 | 11/2015 | Parker et al. | |

FOREIGN PATENT DOCUMENTS

| KR | 20100087425 A | 8/2010 |
|---|---|---|
| KR | 20120118215 A | 10/2012 |
| WO | 2005011991 A1 | 2/2005 |
| WO | 2011141878 A1 | 11/2011 |

OTHER PUBLICATIONS

NailPro Magazine, "How to Master Nail Stamping" <https://www.nailpro.com/stamping-tips>; Dec. 31, 2015 (Year: 2015).*
Parnell et al., Continuously Tuneable Optical Filters from Self-Assembled Block Copolymer Blends, Journal, Soft Matter, 2011, pp. 3721-3725, (7), The Royal Society of Chemistry.
DUMÉ, Photonic Gyroids Mimic Butterfly Wings, Article, May 13, 2016, 3 pages, nanotechweb.org/cws/article/tech/64982.
Zhu et al., Flexible Photonic Metastructures for Tunable Coloration, Letter, Optica, Mar. 2015, pp. 255-258, vol. 2 (3), Optical Society of America.
International Search Report and Written Opinion of the International Searching Authority dated Apr. 5, 2018 in corresponding International Application No. PCT/US2017/067720, filed Dec. 20, 2017, 19 pages.

* cited by examiner

*Primary Examiner* — Nicole P Babson
(74) *Attorney, Agent, or Firm* — Christensen O'Connor Johnson Kindness PLLC

(57) ABSTRACT

A dye-free nail varnish that is used alone or with a stamp to generate a colored coating under incident white light is presented. The nail varnish includes photonic particles and/or block copolymers that can self-assemble to provide a structurally colored coating. The stamp presents a pattern of repeating nanostructures that can be transferred by imprinting the stamp on a coating of a dye-free nail varnish, thereby providing a structurally colored nail varnish coating. Thus, the nail varnish and stamp, independently or together, provide structurally colored coatings without the use of dyes or pigments.

43 Claims, 5 Drawing Sheets

US 10,362,850 B2

DYE-FREE NAIL VARNISH COMPOSITIONS AND METHODS THEREOF

SUMMARY

In an aspect, the present disclosure features a nail varnishing system, including a nail varnish composition including a plurality of photonic particles, a block copolymer, or both a plurality of photonic particles and a block copolymer; and a stamp including a pattern of repeating photonic nanostructures, wherein the stamp is configured to transfer the pattern of repeating photonic nanostructures to a coating of the nail varnish composition.

In another aspect, the present disclosure features a nail vanishing kit, including precursors to a stamp; a stamp mold including a pattern of repeating photonic nanostructures; and a nail varnish composition.

In yet another aspect, the present disclosure features a method of forming a colored nail varnish coating on a nail surface, including applying a coating of a nail varnish composition onto a fingernail or toenail surface, applying a stamp including a pattern of repeating photonic nanostructures to the coating of nail varnish composition to transfer the pattern of repeating photonic nanostructures to the coating of the nail varnish composition, curing the coating of the nail varnish composition; and removing the stamp from the cured coating of nail varnish composition to provide a nail varnish coating including a periodic light-diffractive repeating pattern configured to produce a structural color under incident white light.

In yet a further aspect, the present disclosure features a method of forming a nail varnish coating on a nail surface, including providing a first agent and a second agent to a stamp mold to form a stamp including a pattern of repeating photonic nanostructures; removing the stamp from the mold; applying the stamp to a coating of an uncured nail varnish composition on a fingernail surface or a toenail surface to provide a nail varnish coating including repeating photonic nanostructures.

The summary above is provided to introduce a selection of concepts in a simplified form that are further described below in the Detailed Description. This summary is not intended to identify key features of the claimed subject matter, nor is it intended to be used as an aid in determining the scope of the claimed subject matter.

DESCRIPTION OF THE DRAWINGS

The foregoing aspects and many of the attendant advantages of this disclosure will become more readily appreciated as the same become better understood by reference to the following detailed description, when taken in conjunction with the accompanying drawings, wherein.

DETAILED DESCRIPTION

Figure 1:
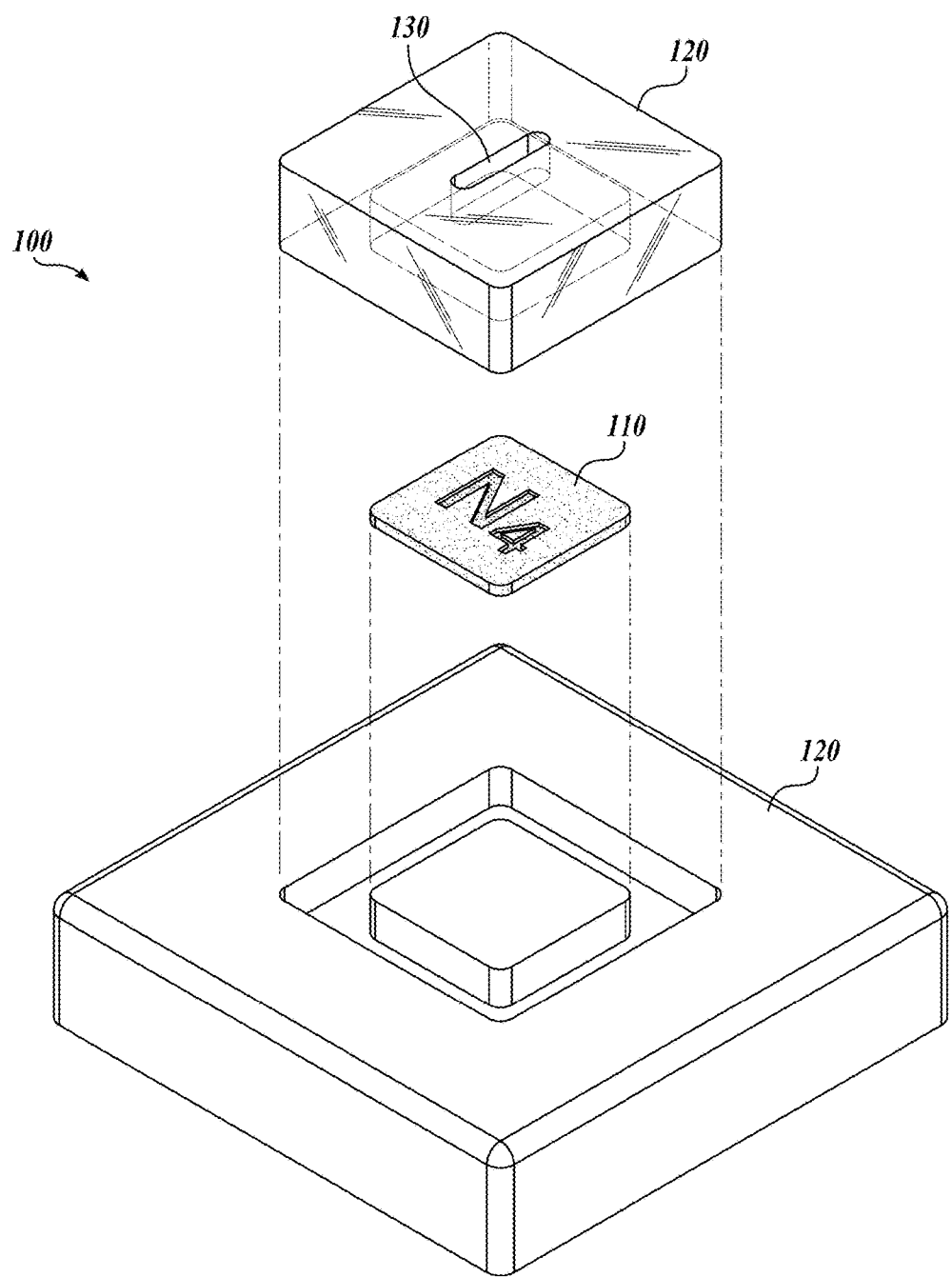
FIG. 1 is a photograph of an embodiment of a stamp mold and a microstructured pattern for insertion into the mold.

In an embodiment, the present disclosure features a dye-free nail varnish that is used alone or with a stamp to generate a structurally colored coating under incident white light. The nail varnish includes photonic particles and/or block copolymers that can self-assemble to provide a structurally colored coating. In an embodiment, the stamp presents a pattern of repeating photonic nanostructures that can be transferred by imprinting the stamp on a coating of a dye-free nail varnish, thereby providing a structurally colored nail varnish coating. In an embodiment, a nail varnish coating including photonic particles and/or block copolymers is used with surface patterns of repeating photonic nanostructures transferred from the stamp to provide one or more structural colors in the coating. In certain embodiments, the dye-free nail varnish and/or the stamp-transferred surface pattern of photonic nanostructures are used on a patterned nail surface, such as an etched nail surface having a pattern of photonic nanostructures that is the same or different from the stamp-transferred surface pattern, to provide a structurally colored nail surface having one or more structural colors under incident white light.

Thus, the present disclosure features a transparent nail varnish and a stamp that, independently or together, provide structurally colored coatings without the use of dyes or pigments.

Definitions

As used herein, "dye-free" refers to a composition that does not include dyes or pigments. In an embodiment, a nail varnish composition is substantially (i.e., greater than 99% by weight, greater than 99.5% by weight, greater than 99.9% by weight, or 100%) dye-free.

As used herein, "structural color" refers to color produced by microscopically structured surfaces fine enough to interfere with incident white light, without the use of pigments or dyes. The color results from, for example, interference effects, which is created by a range of photonic mechanisms, including diffraction gratings, selective mirrors, photonic crystals, crystal fibers, matrices of nanochannels and proteins that can vary their configuration.

As used herein, "photonic" refers to the manipulation and control of light.

As used herein, "photonic nanostructure" refers to a structure on the nanometer scale (e.g., from 1 nm to 1000 nm) that manipulates and controls light.

As used herein, "white light" refers to an electromagnetic radiation balance between the entire visible spectrum from violet to red (i.e., a mixture of all the wavelengths of the visible spectrum), which provides the perception that the light is white.

As used herein, "visible light" or "visible spectrum" refers to a wavelength band ranging from 400 to 700 nm of the electromagnetic radiation spectrum, visible to the human eye.

As used herein, "metamaterials" refer to synthetic composite materials with structures that exhibit properties not usually found in natural materials, for example, a negative refractive index. As an example, a metamaterial is a material having a repeating pattern at scales that are smaller than the wavelengths of the phenomena they influence, such as a given wavelength of visible light. In an embodiment, the metamaterial has a pattern of repeating photonic nanostructures, such as a pattern of repeating parallel grooves, surface gratings, juxtaposed rings, cylindrical elements, rods that are arranged in parallel geometry that provide hexagonal symmetry, or gyroid photonic nanostructures.

As used herein, "metastructure" refer to the structure of a metamaterial. For metamaterials that influence visible light, the metastructure is a repeating pattern of photonic nanostructures, e.g., periodic photonic nanostructures.

Dye-free nail varnish compositions

The nail varnish of the present disclosure can be a solvent-based or a photocurable composition. In an embodiment, the nail varnish includes a plurality of photonic particles and/or a block copolymer, which can self-organize to form patterns of photonic nanostructures that provide a structurally colored nail varnish coating under incident white light. In another embodiment, the coating of nail varnish includes a pattern including a plurality of photonic particles, a block copolymer, or both a plurality of photonic particles and a block copolymer; the coating of nail varnish includes a surface pattern of photonic nanostructures (e.g., imprinted by the stamp) that together provide a nail varnish coating having one or more structural colors under incident white light. In an embodiment, the nail varnish coating and/or the stamp are used in conjunction with a nail that has been etched with a pattern of photonic nanostructures to provide one or more structural colors under incident white light. Etched nail surfaces that can be used together with the nail varnish compositions and/or stamps of the present disclosure are described, for example, U.S. patent application Ser. No. 15/402,681, entitled "Devices and Methods for Non-Planar Photolithography of Nail Polish," and filed Jan. 10, 2017, herein incorporated by reference in its entirety.

The nail varnish compositions of the present disclosure can include a plurality of photonic particles and/or one or more block copolymers. In an embodiment, the photonic particles are monodisperse and form a colloidal crystal which appears colored to a human eye. The observed color depends on two main factors: the lattice spacing and the refractive index of the particles and the matrix which affects the wavelength of the diffracted light.

In an embodiment, the photonic particles have a maximum particle dimension of from 250 nm (e.g., from 300 nm, from 350 nm, from 400 nm, from 500 nm) to 550 nm (e.g., to 510 nm, to 500 nm, to 400 nm, from 350 nm, or to 300 nm). Examples of materials for photonic particles include metal (e.g., gold, copper, and/or silver), metal oxide (e.g., $Al_2O_3$, $TiO_2$, $SnO_2$, $Fe_2O_3$, $ZrO_2$, $CeO_2$, and $Y_2O_3$), metal chalcogenide, metal pnictide, silica, polymers (e.g., latex, acrylic, polystyrene, poly(vinyl acetate), polyacrylonitrile, poly(styrene-co-butadiene), polyester, polyamides, polyurethane, poly(methylmethacrylate), poly(N-isopropylacrylamide), poly(fluoromethylmethacrylate)), and/or synthetic melanin. Examples of suitable materials for photonic particles are provided, for example, in U.S. Publication 2010/0040741, incorporated herein by reference in its entirety.

In an embodiment, the monodisperse photonic particles are inorganic or organic particles. In an embodiment, the nail varnish composition includes monodisperse particles and at least one polymer precursor, such as those described, for example, in U.S. Pat. Nos. 5,985,951; 8,399,537; 8,901,199; and 5,637,292; and U.S. Publication No. 2012/276028; and at least one polymerization initiator, such as a photoinitiator described, for example, in U.S. Pat. Nos. 5,985,951 and 8,399,537, each of which is incorporated herein in its entirety.

In an embodiment, the nail varnish composition includes one or more block copolymers. Examples of block copolymers are described, for example, in Parnell et al., Soft Matter, 2011, 7, 3721-3725, herein incorporated by reference in its entirety. In an embodiment, the block copolymer is one or more of poly(styrene-b-isoprene) diblock copolymer, poly(styrenesulfonate-methylbutylene), and polystyrene-poly(2-vinylpyridine).

In an embodiment, the nail varnish composition includes block copolymers such as two symmetric high molecular weight poly(styrene-b-isoprene) (PS-b-PI) diblock copolymers. The two (PS-b-PI) block copolymers can have a weight average molecular weight ($M_w$) of about 560 kg/mol and 1000 kg/mol respectively, and a PS:PI ratio of 55:45 and 40:60, respectively. In some embodiments, the two (PS-b-PI) block copolymers have polydispersity indices of about 1.2. In an embodiment, the polymer blends are dissolved in a nonselective solvent (e.g., xylene) before application to a substrate, such as a nail or fake nail surface. A change in structural color can be obtained by with a variation of the blend composition ratio. Without wishing to be bound by theory, the structural color of the blends is believed to be due to the internal structure of the sheared blend solutions reflecting a narrow and well-defined distribution of wavelengths.

In an embodiment, the one or more block copolymers form lamellae when self-organized in a nail varnish coating. The lamellar domain spacing can be in the range from 120 nm (e.g., 130 nm, 150 nm, 175 nm, 200 nm, 225 nm, or 250 nm) to 260 nm (e.g., 250 nm, 225 nm, 200 nm, 175 nm, 150 nm, or 130 nm). The self-organization results in nanometer-ranged structures.

In an embodiment, the emission maximum of the reflected visible light for a coating of nail varnish of the present disclosure, having photonic particles and/or block copolymers, is 400 nm or more (e.g., 450 nm or more, 500 nm or more, 550 nm or more, 600 nm or more, 650 nm or more, 700 nm or more, or 800 nm or more) and/or 850 nm or less (e.g., 800 nm or less, 700 nm or less, 650 nm or less, 600 nm or less, 550 nm or less, 500 nm or less, or 450 nm or less), under incident white light. In an embodiment, the emission maximum of the reflected visible light for a coating of nail varnish of the present disclosure is from 400 nm to 700 nm under incident white light. In some embodiments, the full width half maximum of the emission is 8 nm or more (e.g., 10 nm or more, 15 nm or more, 20 nm or more, 30 nm or more, or 40 nm or more) and/or 50 nm or less (e.g., 40 nm or less, 30 nm or less, 20 nm or less, 15 nm or less, or 10 nm or less).

As discussed above, the nail varnish compositions of the present disclosure are dye-free, i.e., the compositions do not include colored dyes or pigments. Non-limiting examples of dyes that the nail varnish compositions do not include are Sudan red, DC Red 17, DC Green 6, β-carotene, soybean oil, Sudan brown, DC Yellow 11, DC Violet 2, DC Orange 5 and quinoline yellow. Non-limiting examples of pigments that the nail varnish compositions do not include are white or colored pigments, inorganic and/or organic pigments, and coated or uncoated pigments. For example, the nail varnish compositions do not include inorganic pigments such as titanium dioxide, optionally surface treated, zirconium or cerium oxides and iron or chromium oxides, manganese violet, ultramarine blue, chromium hydrate and ferric blue; organic pigments of carbon black, pigments of D & C type and lakes based on cochineal carmine or on barium, strontium, calcium or aluminum, such as D&C Red No. 10, 11, 12, and 13, D&C Red No. 7, D&C Red No. 5 and 6, and D&D Red No. 34, as well as lakes such as D&C Yellow Lake No. 5 and D&C Red Lake No. 2.

The nail varnish compositions of the present disclosure do not include pearlescent pigments such as white pearlescent pigments, including mica covered with titanium oxide or with bismuth oxychloride, colored pearlescent pigments, including titanium oxide-coated mica with iron oxides, titanium oxide-coated mica with in particular ferric blue or chromium oxide, or titanium oxide-coated mica with an organic pigment of the abovementioned type, and pearlescent pigments based on bismuth oxychloride.

Stamp

In an embodiment, a pattern of photonic nanostructures is transferred using a stamp (e.g., a flexible stamp) to an underlying coating of the nail varnish, by pressing a stamp to a coating of the nail varnish after application of the nail varnish to a nail surface, and before or during curing the nail varnish. After removal of stamp, the coating of the nail varnish can have a pattern of photonic nanostructures that generate a structural color in the visible spectrum, under incident white light. The stamp is disposable or reusable.

In an embodiment, a stamp transfers a pattern of repeating photonic nanostructures present on a hard mold onto a wet surface of a nail varnish coating. The nail varnish coating cures in the presence of stamp. After curing the nail varnish coating and removal of the stamp, the pattern is embedded on the cured coating surface.

In an embodiment, the stamp is a flexible stamp formed of a flexible material. An example of a flexible polymer is a silicone elastomer, which is transparent to UV light and highly permeable to vapor. Without wishing to be bound by theory, it is believed that there is an absence of C=C bonds in a silicone elastomer, which absorb in the UV spectrum. Silicone elastomer is also a low surface free energy material, making it a low adherence material.

The stamp can be used with photocurable (e.g., ultraviolet light-curable, or UV-curable) nail varnish compositions and/or with solvent-based nail varnish compositions. In an embodiment, a silicone elastomer stamp is used to transfer a pattern of repeating photonic nanostructures to a photo-curable nail varnish coating. The coating of the nail varnish hardens after exposure to UV light. The pattern is imprinted onto the nail varnish coating during the curing process, after exposure of the photocurable nail varnish to UV light. The silicone elastomer stamp is then removed from the cured nail coating surface leaving the micro-structured pattern.

In another embodiment, for a solvent-based nail varnish coating, a solvent vapor-permeable stamp, such as a silicone elastomer stamp, is used. The solvent vapor-permeable stamp allows the nail varnish coating to dry while imprinting a pattern of repeating photonic nanostructures on the coating surface. The stamp is then removed and optionally reused.

Once the pattern of repeating photonic nanostructures is transferred, the cured nail varnish (whether photocurable or cured by solvent removal/evaporation) includes a periodic light-diffractive repeating pattern that produces visible structural color under incident white light.

In an embodiment, the stamp is formed of a material such as silicone (e.g., silicone elastomer), polycarbonate (e.g., from a step growth polymerization of bisphenol A and phosgene), Butivar (e.g., polyvinyl acetals prepared from aldehydes and polyvinyl alcohols), fluoropolymers, polymethylpentene (TPX) (e.g., from Ziegler-Natta type catalysis of 4-methyl-1-pentene), and/or cyclic olefin copolymers (e.g., from copolymerization of cycloolefin with ethylene or α-olefin). In an embodiment, the stamp is formed from a silicone elastomer.

In an embodiment, when a silicone elastomer is used for the stamp, the stamp is made at room temperature with the use of a silicone elastomer kit, such as Sylgard® 184 from Aldrich/Dow Corning. In an embodiment, the kit includes two containers. In an embodiment, the first container includes Sylgard® 184A and the second container includes Sylgard® 184B. The containers include vinyl end-capped oligomeric dimethyl siloxane, a methyl hydrosiloxane as crosslinking agent, and a platinum complex as a catalyst for the hydrosilation reaction. In an embodiment, the platinum complex is contained in both containers, the first container includes vinyl end-capped oligomeric dimethyl siloxane and the second container includes the methyl hydroxysiloxane. In an embodiment, the vinyl end-capped oligomeric dimethyl siloxane and the methyl hydroxysiloxane are configured to polymerize to provide a silicone elastomer when in contact with one another in the presence of a platinum catalyst. In an embodiment, Sylgard® 184A and Sylgard® 184B contain 30-60 and 10-30 wt %, respectively of dimethylvinylated and trimethylated silica fillers. In an embodiment, a 10:1 Sylgard® 184A and Sylgard® 184B mixture by mass is used to make a silicone elastomer stamp.

Once the initial mold is chosen, the seals of the silicone stamp precursor containers are broken to mix the materials from the two containers together. After mixing of the two liquids, the mixture is poured into the mold and cured at room temperature. Once the silicone elastomer has fully reacted, the resulting stamp is removed from the initial mold. In an embodiment, this silicone stamp is used multiple times on a photo-curable or solvent-based nail varnish coating to provide a photonic nanostructure-patterned coating. A structural color can result on the nail varnish coating when the patterns on the nail varnish coating interact with incident white light, for example, through refraction, interference, diffraction, and/or scattering.

In an embodiment, the molds for the stamps of the present disclosure provide a variety of repeating photonic nanostructures and/or three-dimensional effects, giving volume and unique color effects to the nail varnish coating. In an embodiment, the molds are purchased or printed using, for example, a smart phone 3D printer such as OLO.

Pattern

Without wishing to be bound theory, it is believed that the pattern of repeating photonic nanostructures on or in a nail varnish coating has a relatively high periodicity to provide one or more bright structural colors. The periodicity and the spatial dimension can range from a few thousand nanometers (i.e., several microns, up to 3.4 microns, up to 2 microns, up to 1 micron) to a few hundred nanometers. In an embodiment, the stamp, the photonic particles, and/or the block copolymer, have or form a plurality of regularly repeating photonic nanostructures (e.g., pixels), the spacing between two repeating structures have a maximum dimension of 1000 nm or less (e.g., 900 nm or less, 800 nm or less, 700 nm or less, 600 nm or less, 500 nm or less, 400 nm or less, 300 nm or less, or 200 nm or less) and/or 100 nm or more (e.g., 200 nm or more, 300 nm or more, 400 nm or more, 500 nm or more, 600 nm or more, 700 nm or more, 800 nm or more, or 900 nm or more).

In an embodiment, the pattern of repeating photonic nanostructures extends for a length of 0.4 mm or more (e.g., 0.5 mm or more, 1 mm or more, 5 mm or more, 1 cm or more, or 2 cm or more) and/or 3 cm or less (e.g., 2 cm or less, 1 cm or less, 5 mm or less, 1 mm or less, or 0.5 mm or less). For example, the pattern of repeating photonic nanostructure extends the length and/or width of a nail on which the nail varnish is applied.

Without wishing to be bound by theory, it is believed that the structural color on or in the nail varnish coating results from an interference and/or a diffraction of incident white light from the periodic patterns on or in a nail varnish coating. The patterns can take the form of, for example, parallel grooves, surface gratings, juxtaposed rings, cylindrical elements, or rods that are arranged in parallel geometry that provide hexagonal symmetry. In an embodiment, the patterns on or in a nail varnish coating are repeating photonic gyroid nanostructures, for example, as described in nanotechweb.org/cws/article/tech/64982, herein incorporated by reference in its entirety. As discussed above, in an embodiment, the photonic particles and/or the block copolymers form the photonic patterns in a nail varnish coating. In another embodiment, the stamp imprints a photonic pattern on a nail varnish coating. In yet an embodiment, the nail surface is etched with a pattern of photonic nanostructures, the photonic particles and/or the block copolymers form the photonic patterns in a nail varnish coating, and the stamp imprints a photonic pattern on a nail varnish coating; the patterns on the nail, in a nail varnish coating, and imprinted on a nail varnish coating, can be the same or different. In an embodiment, the nail varnish coating is configured to change color if coating is flexed due to changes in a periodicity of the repeating photonic nanostructures in the coating.

In an embodiment, the photonic particles include one or more repeating surface features, such as ridges, that are sized and configured to reflect a specific wavelength of light to provide structural color to a nail varnish coating. Examples of surface ridges are described, for example, in Zhu et al., Optica, (2015), 2(3), 255-258, incorporated herein by reference in its entirety.

In an embodiment, the pattern imprinted onto the transparent nail varnish coating, or embedded in the nail varnish coating transparent film has a photonic structure that produces structural color in the visible light range under incident ambient white light. Without wishing to be bound by theory, it is believed that the observed colors depend mainly on the pattern spacing and the refractive index of the two matrixes. Here, the first matrix is the nail varnish (dried nail polish refractive index~1.42) and the second matrix is air (refractive index air=1, for a nail varnish coating with no top coat). The reflection wavelength from the photonic structure with alternative refractive indices is determined by the optical path lengths:

$$\text{lambda} = 2(n1*d1 + n2*d2) \quad \text{Equation (1)}$$

where n1 and n2 are the refractive indexes and d1 and d2 are the thicknesses of the domains.

Other nail varnish components

The nail varnish composition of the present disclosure is generally prepared by mixing a photonic particle or a block copolymer with a final lacquer formulation.

In an embodiment, the nail varnish composition includes a solvent, such as a volatile organic solvent selected from butyl acetate, ethyl acetate, acetone, isopropanol, ethanol, and/or n-propyl acetate. In some embodiments, for a photocurable nail varnish composition, the nail varnish composition is neat, where the reactive monomers (such as methacrylate monomers) are themselves liquid and do not include additional organic solvents.

In an embodiment, the nail varnish composition includes one or more of the following: (1) a solvent-insoluble protective colloid capable of decreasing flocculation of the particles and which is compatible with a film former present in the lacquer composition; and (2) a plasticizer, having low volatility and which is both compatible with the protective colloid as well as the film former used in the final coating composition.

In an embodiment, the protective colloid is sufficiently soluble in the plasticizer and is compatible with cellulose nitrate or other desired film forming agents present in the lacquer composition.

Representative chemical groups of protective colloids include: saccharide based polymers, acrylic polymers, polyesters, alkyd resins, polyamides, cellulosic polymers, sulfonated naphthalenes, vinyl polymers, formaldehyde condensates, polyurethanes, substituted pyrrolidone polymers, and polypropylene oxides. Further examples of protective colloids include toluene sulfonamideformaldehyde condensates (for example Monsanto's SANTOLITE MHP), methyl-butyl methacrylate copolymer (Rohm & Haas' Acryloid B-66"), sucrose benzoate, ethyl cellulose, dimer acid based polyamide resin (Henkel's Versamide 940) and polymeric esterified pentaerythritol (Hercules' Herco-Flex 900).

Generally, the amount of protective colloid utilized in the nail varnish composition is that which is necessary to decrease agglomeration or flocculation of the photonic particles. In an embodiment, the protective colloid is present in amounts ranging from about 2.0% to about 25.0% by weight.

Examples of plasticizers include abietic acid derivatives, acetic acid derivatives, adipic acid derivatives, azelaic acid derivatives, benzoic acid derivatives, polyphenyl derivatives, citric acid derivatives, epoxy derivatives, proprietary esters, ether derivatives, formal derivatives, glutaric acid derivatives, glycerol derivatives, glycol derivatives, linear dibasic acid derivatives, petroleum derivatives, isobutyric acid derivatives, isophthalic acid derivatives, lauric acid derivatives, mellitates, myristic acid derivatives, nitrile derivatives, oleic acid derivatives, palmitic acid derivatives, paraffin derivatives, pelargonic acid derivatives, pentaerythritol derivatives, phosphoric acid derivatives, phthalic acid derivatives, polyesters, ricinoleic acid derivatives, sebacic acid derivatives, stearic acid derivatives, styrene derivatives, sucrose derivatives, sulfonic acid derivatives, terephthalic acid derivatives, tartaric acid derivatives, carbonic acid derivatives, aconitic acid derivatives, maleic acid derivatives, fumaric acid derivatives, capyrylic acid derivatives, butyric acid derivatives as well as camphor and castor oil.

In an embodiment, the plasticizer includes N-ethyl toluene sulfonamide (Santicizer 8), butyl benzyl phthalate (Santicizer S160), alkyl sulphonic esters of phenol e.g., "Mesamoll" (Mobay Chemical Co.) and/or tricresyl phosphate.

In an embodiment, the amount of plasticizer is an amount ranging from about 75% to about 98% by weight.

In an embodiment, one or more surfactants are included in the nail varnish composition. When present, the amount of surfactant(s) can range from about 0.1% to about 5.0%. Suitable surfactants include anionic, cationic, nonionic or amphoteric surfactants. Examples of suitable anionic surfactants include the saponification products of fats, sulfated fatty acid esters, sulfated fatty amides, sulfated fatty alcohols, phosphate esters of fatty alcohol, amino caboxylated acids, sulfated rosin and sulfated nonionic type surfactants. Examples of cationic surfactants include aliphatic amines with fatty chains and quaternary ammonium salts. Examples of nonionic surfactants include polyoxyethylene alkylphenols, polyoxyethylene alcohols, polyoxyethylene esters of fatty acids, polyoxyethylene alkyl amines, polyoxyethylene alkylimides, polyol surfactants, polyalkylene oxide block copolymers, propoxylated surfactants, and fluorinated alkyl esters. In an embodiment, examples of surfactants include Nalco 2395 and Troykyd Solvent Anticrater 366.

The lacquer formulation of the nail varnish composition includes a suitable film forming agent and various optional ingredients including: one or more modifying resins, thinners, solvents, diluents, surfactants, flocculating agents or suspending agents. Examples of film formers include: cellulose nitrate, nitrocellulose, cellulose propionate, cellulose acetate butyrate, ethyl cellulose, sucrose acetate isobutyrate, vinyl polymers, e.g. polyvinyl acetate and polyvinyl alcohol, acrylic resins, e.g. acrylic polymers (thermoplastic acrylic esters, homopolymers and copolymers of alkyl acrylates and methacrylates), urethane polymers, nylon, polyesters, and polyalkyds.

The amount of the film forming agent present in the lacquer formulation generally ranges from about 2.0% to about 40.0%.

The optional modifying resin or resins present in the lacquer formulation are compatible with the desired film forming agent. The primary role of a modifying resin is to impart one or more of the following properties to the final composition: improved gloss, improved depth of gloss, improved adhesion, improved film hardness, reduced film shrinkage, improved water resistance and increased solids. Examples of modifying resins include toluene sulfonamide formaldehyde condensates (Santolite MHP and/or Santolite MS-80); sucrose benzoate; sucrose acetate isobutyrate, copolymeric mixtures thereof, alkyds, polyvinyl acetate, polyesters, acrylics, formaldehyde condensates, nylon, Rosin resins, acetates and cyclohexahones. Further examples of modifying resins include either or both Santolite MHP and Santolite MS-80 (80.0% solution) and Cellovar CV-160 (80.0% solution in butyl acetate) i.e., sucrose benzoate/sucrose acetateisobutyrate copolymer.

The amount of the total modifying resin or mixtures thereof present in the lacquer formulation ranges from 0.0% to about 50.0% (e.g., from about 4.0% to about 13.0%), based on 100% solids.

Kits and methods of use

In an embodiment, the present disclosure features a nail varnishing kit that includes precursors to a stamp, a stamp mold including a pattern of repeating photonic nanostructures; an optional ultraviolet light source; and a nail varnish composition.

In an embodiment, the precursors to a stamp are provided in two parts. In an embodiment, the precursors include vinyl end-capped oligomeric dimethyl siloxane, a methyl hydrosiloxane as crosslinking agent, and a platinum complex as a catalyst for the hydrosilation reaction. In an embodiment, the platinum complex is provided in one part and does not contact the reagents in a second part until the two-part precursors are mixed together. In an embodiment, the two part-precursors are Sylgard® 184A and Sylgard® 184B. In an embodiment, Sylgard® 184A and Sylgard® 184B contain 30-60 and 10-30 wt %, respectively of dimethylvinylated and trimethylated silica fillers. In an embodiment, a 10:1 Sylgard® 184A and Sylgard® 184B mixture by mass is used to make the silicone elastomer stamp in the kit.

In an embodiment, in a 2-part precursor mixture, the components that react together are the vinyl end-capped oligomeric dimethyl siloxane and the methyl hydroxysiloxane (the cross linking agent), and a platinum catalyst is present in both parts. The first part includes the vinyl end-capped oligomeric dimethyl siloxane and the second part includes the methyl hydroxysiloxane. Once mixed together and in contact with one another, the two parts react together and polymerize to provide the silicone elastomer. In an embodiment, the first part is provided in a first container, and the second part is provided in a second container. In use, in an embodiment, the first and second precursor parts are mixed immediately prior to use and poured into the stamp mold.

In an embodiment, the stamp is made of a polycarbonate, which can be formed from bisphenol A and phosgene or carbonic acid precursors. In an embodiment, the stamp is formed of polyvinyl acetals, the precursors of which are polyvinyl alcohols and aldehydes. An example of a polyvinyl acetal is Butivar. In an embodiment, the stamp is formed of fluoropolymers. In an embodiment, the stamp is formed of polymethylpentene, the precursors of which are 4-methylpent-1-ene and a Ziegler-Natta catalyst. In an embodiment, the stamp is formed of cyclic olefin copolymers, the precursors of which are cyclic olefin and ethylene or alpha olefin. In an embodiment, the precursors to each of the polymers above are provided in separate containers. In an embodiment, a stamp is formed from any of the polymer above, and a photonic pattern is etched or formed by injection molding on the stamp. The stamp including the photonic pattern is then provided in a kit.

Figure 2A:
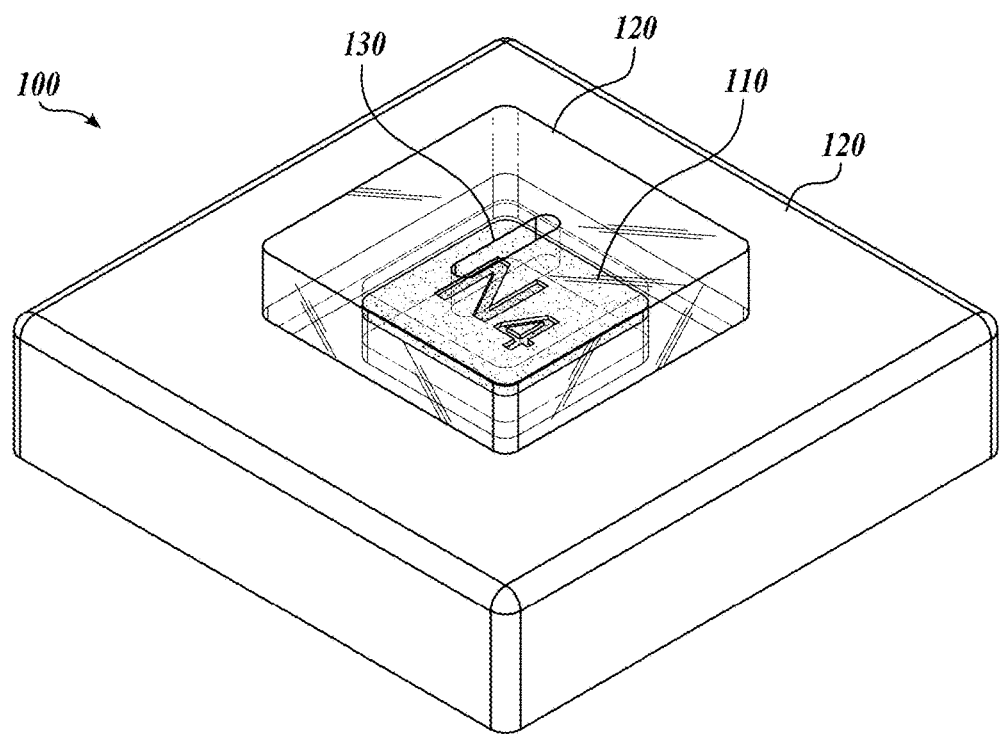
FIG. 2A is a photograph of an embodiment of an assembled mold including a microstructured pattern and a silicone mixture.
Figure 2B:
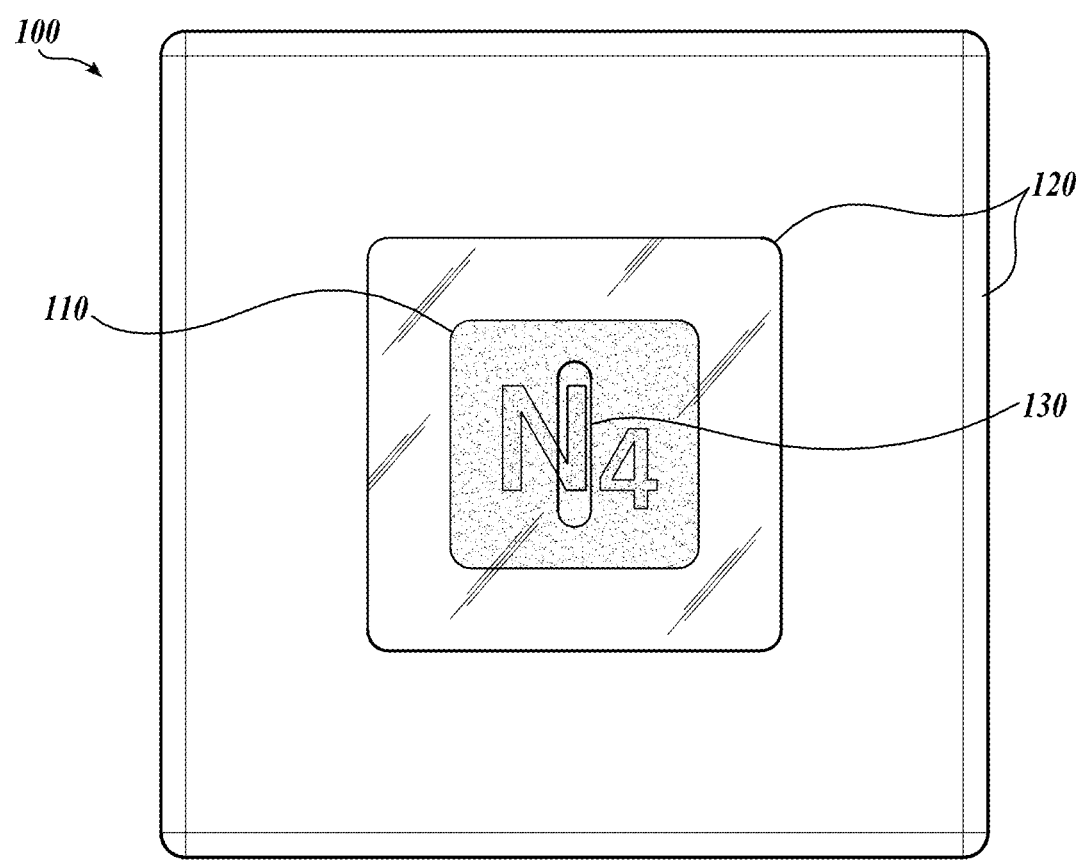
FIG. 2B is a photograph of an embodiment of an assembled mold including a microstructured pattern and a silicone mixture.

In an embodiment, the kit includes a stamp mold. Referring to FIG. 1, in an embodiment, the mold 100 includes interchangeable patterns of photonic nanostructures 110 that are placed in a master container 120. Referring to FIGS. 2A and 2B, when assembled, master mold 120 holds pattern 110 within a compartment, which has a port 130 for introduction of a polymer precursor mixture.

Figure 3A:
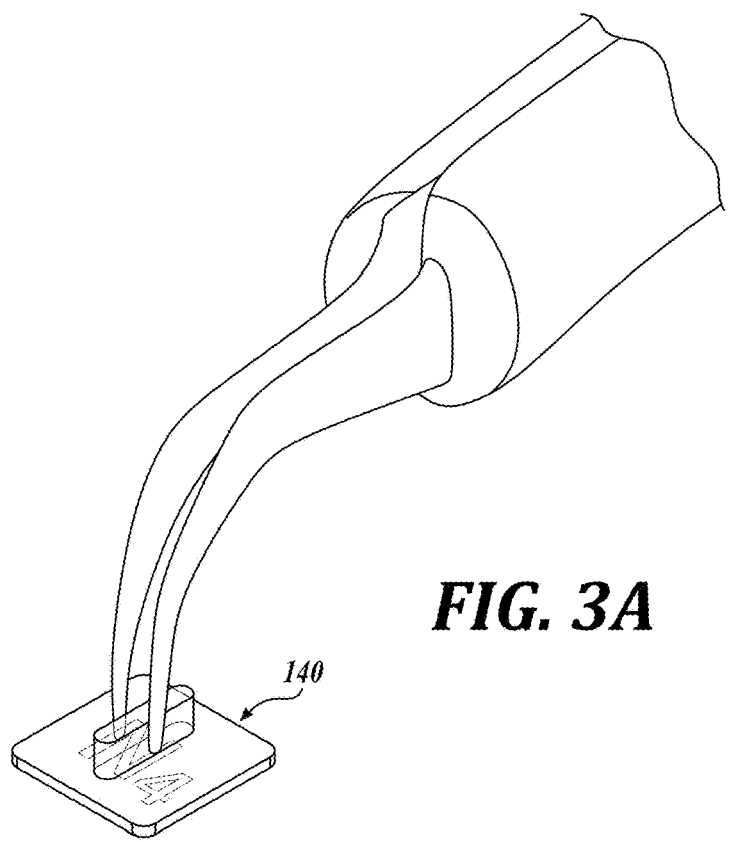
FIG. 3A is a photograph of an embodiment of a silicone stamp formed in the assembled mold of FIGS. 2A and 2B.
Figure 3B:
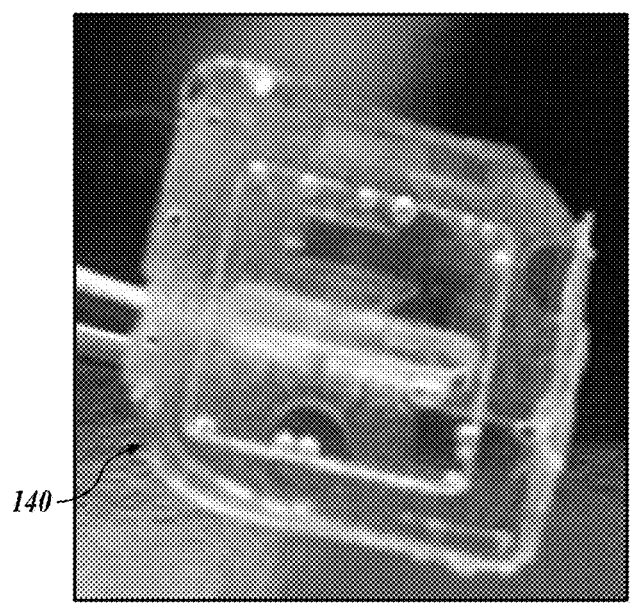
FIG. 3B is a photograph of an embodiment of a silicone stamp formed in the assembled mold of FIGS. 2A and 2B.

Once the polymer precursor mixture has polymerized, master mold 120 is opened and the stamp 140 having the reverse image of interchangeable pattern 110 is removed, as shown, for example, in FIGS. 3A and 3B. In an embodiment, interchangeable pattern 110 is reusable and can be removed from master mold 100.

Figure 4A:
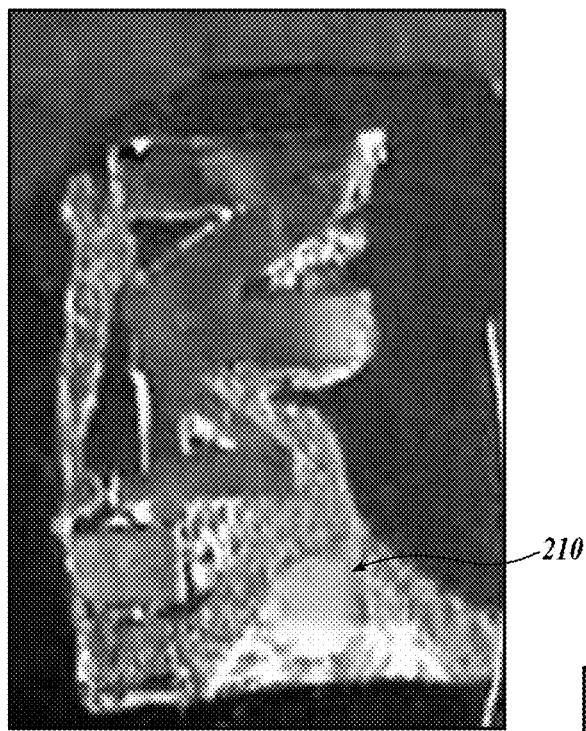
FIG. 4A is a photograph of a cured coating of a solvent-based nail varnish stamped with the silicone stamp of FIGS. 3A and 3B.
Figure 4B:
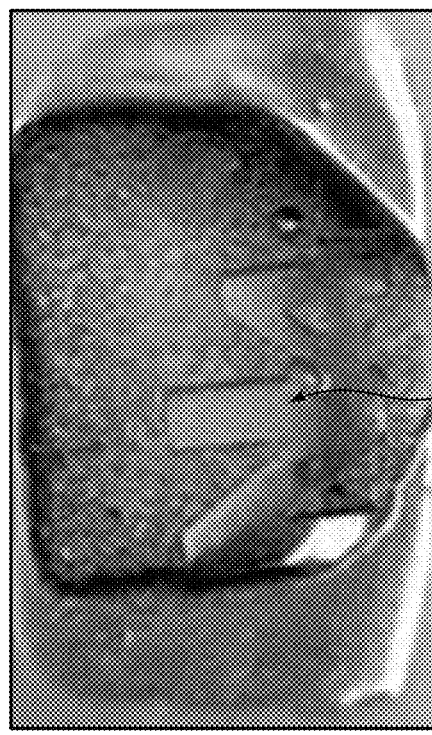
FIG. 4B is a photograph of a cured coating of a UV-curable nail varnish stamped with the silicone stamp of FIGS. 3A and 3B.

As discussed above, in an embodiment, stamp 140 is used to transfer the image of interchangeable 110 onto a coating of a nail varnish composition on a nail surface, which is cured by exposure to UV light or by evaporation of a solvent in the coating of nail varnish composition, depending on whether the nail varnish composition is photo-curable or solvent-based. When the coating of nail varnish composition is cured, stamp 140 is removed from the coating to provide either a patterned nail varnish coating exhibiting a structural color under incident white light. FIG. 4A shows an embodiment of a patterned nail varnish coating 210 using a solvent-based nail varnish composition, exhibiting a structural color under incident white light. FIG. 4B shows an embodiment of a patterned nail varnish coating 220 using a photo-curable nail varnish composition, exhibiting a structural color under incident white light.

Thus, in an embodiment, the present disclosure provides a method of forming a colored nail varnish coating on a nail surface, including applying a coating of an uncured nail varnish composition onto a fingernail or toenail surface, applying a stamp including a pattern of repeating photonic nanostructures to the coating of the uncured nail varnish composition to transfer the pattern of repeating photonic nanostructures to the coating of the uncured nail varnish composition, curing the coating of the uncured nail varnish composition (e.g., by exposing the nail varnish composition to ultraviolet light, by evaporating a solvent in the nail varnish composition); and removing the stamp from the cured coating of nail varnish composition to provide a nail varnish coating including a periodic light-diffractive repeating pattern configured to produce visible structural color under incident white light. In an embodiment, the underlying fingernail or toenail surface includes an etched photonic pattern, which produces visible structural color under incident white light. In an embodiment, the etched photonic pattern on the fingernail or toenail surface together with the nail varnish coating that includes a period light-diffractive repeating pattern produce one or more structural colors under incident white light.

In another embodiment, the present disclosure provides a method of forming a nail varnish coating on a nail surface, including providing a mixture of a first agent and a second agent to a stamp mold to form a stamp including a pattern of repeating photonic nanostructures; removing the stamp from the mold; applying the stamp to a coating of an uncured nail varnish composition on a fingernail surface or a toenail surface to provide repeating photonic nanostructures on the nail varnish coating. In an embodiment, the first agent is a vinyl end-capped oligomeric dimethyl siloxane, and the second agent is a methyl hydroxysiloxane. In an embodiment, the method further includes curing the coating of the uncured nail varnish composition (e.g., by exposing the nail varnish composition to ultraviolet light, by evaporating a solvent in the nail varnish composition) after applying the stamp to the coating of the uncured nail varnish composition. In an embodiment, the cured nail varnish coating includes a periodic light-diffractive repeating pattern configured to produce visible structural color. In an embodiment, the underlying fingernail or toenail surface includes an etched photonic pattern, which produces visible structural color under incident white light. In an embodiment, the etched photonic pattern on the fingernail or toenail surface together with the nail varnish coating that includes a period light-diffractive repeating pattern produce one or more structural colors under incident white light.

Unless otherwise defined, all technical and scientific terms used herein have the same meaning as commonly understood by one of ordinary skill in the art. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

EXAMPLE

Example 1

Silicone Elastomer Stamp and Formation of Nail Pattern

Stamp manufacture

Referring to FIG. 2B, an initial stamp mold is provided, and the "N4" mother pattern (1.4 cm (length)×1.4 cm (width)×0.2 cm (thickness)) is placed in the stamp mold. A top piece (2.5 cm (length)×2.5 cm (width)×0.7 cm (thickness)) is then placed over the mother stamp.

A Sylgard® 184 elastomer mixture in two parts (Sigma Aldrich) in a ratio of 10:1(monomer : curing agent) by weight was mixed together. Once well mixed, the mixture was poured into the mold through a slot (0.1 cm ×0.8 cm) located on the top piece of the mold. The mixture was cured in the mold at room temperature for 48 hours, or at 50 ° C. overnight. The stamp was then removed from the mold to obtain a flexible solid silicone elastomer stamp.

Transferring the surface pattern to nail varnish:

For a UV-curable nail varnish composition: a gel UV nail varnish coating was applied onto a nail plate. The flexible silicone elastomer stamp was then applied to the nail varnish coating. The nail with applied stamp was placed under UV or UV-LED light source for 30 seconds to 2 min. The nail was then removed from the UV light source lamp and the stamp was removed. The cured nail varnish coating had a microstructured pattern which provided a pigment-free color effect to the nail varnish coating.

For a solvent-based nail varnish composition: a nail varnish composition was applied as a coating to the UV-curable nail varnish composition. Before the solvent-based nail polish dries, the silicone stamp was applied to the top of the nail vanish coating. The nail varnish coating was then dried by solvent evaporation through the silicone stamp and the stamp was removed. The dried nail varnish coating had a microstructured pattern which provided a pigment-free color effect to the dried nail varnish coating.

While illustrative embodiments have been illustrated and described, it will be appreciated that various changes can be made therein without departing from the spirit and scope of the disclosure.

The embodiments of the disclosure in which an exclusive property or privilege is claimed or defined as follows:

1. A nail varnishing system, comprising:
a nail varnish composition including a plurality of photonic particles, a block copolymer, or both a plurality of photonic particles and a block copolymer, wherein the block copolymer is selected from a poly(styrene-b-isoprene) diblock copolymer, poly(styrenesulfonate-methylbutylene), and polystyrene-poly (2-vinylpyridine); and
a stamp including a pattern of repeating nanostructures, wherein the stamp is configured to transfer the pattern of repeating nanostructures to a coating of the nail varnish composition to provide a pattern of repeating photonic nanostructures on the coating of the nail varnish composition.

2. The nail varnishing system of claim 1, wherein the stamp is a silicone stamp.

3. The nail varnishing system of claim 1, wherein the plurality of photonic particles, the block copolymer, or both the plurality of photonic particles and the block copolymer self-organize to provide a structural color under incident white light.

4. The nail varnishing system of claim 1, wherein when cured, the coating of the nail varnish composition includes a patterned coating including a plurality of photonic particles, a block copolymer, or both a plurality of photonic particles and a block copolymer.

5. The nail varnishing system of claim 1, wherein the nail vanish composition is configured to be applied to a nail surface including etched photonic nanostructures.

6. The nail varnishing system of claim 1, wherein the photonic particles are configured to form photonic nanostructures including one or more photonic gyroid nanostructures.

7. The nail varnishing system of claim 1, wherein the photonic particles are configured to form one or more photonic nanostructures.

8. The nail varnishing system of claim 1, wherein the block copolymer is configured to form one or more photonic nanostructures.

9. The nail varnishing system of claim 1, wherein the photonic particles include one or more surface ridges configured to reflect a visible light wavelength.

10. The nail varnishing system of claim 1, wherein the nail varnish composition is substantially dye-free.

11. The nail varnishing system of claim 1, wherein the nail varnish composition is dye-free.

12. The nail varnishing system of claim 1, wherein the nail varnish composition includes a plurality of photonic particles and a block copolymer.

13. The nail varnishing system of claim 1, wherein the photonic particles have a particle dimension of from 250 nm to 550 nm.

14. The nail varnishing system of claim 1, wherein the photonic particles include a material selected from metal, metal oxide, metal chalcogenide, metal pnictide, silica, latex, acrylic, polystyrene, poly(vinyl acetate), polyacrylonitrile, poly(styrene-co-butadiene), polyester, polyamides, polyurethane, poly(methylmethacrylate), poly(fluoromethylmethacrylate), synthetic melanin, and poly (N-isopropylacrylamide).

15. The nail varnishing system of claim 1, wherein the block copolymer self-organizes into lamellae, each lamella having a thickness of from 130 nm to 230 nm.

16. The nail varnishing system of claim 1, wherein the stamp includes a pattern of repeating photonic nanostructures extending for a length of at least 0.4 mm, wherein each photonic nanostructure has a dimension of from 100 nm to 1000 nm.

17. The nail varnishing system of claim 1, wherein when the coating of the nail varnish composition is applied and cured on a nail surface, the cured coating includes a periodic light-diffractive repeating pattern configured to produce a structural color under incident white light.

18. The nail varnishing system of claim 17, wherein the periodic light-diffractive repeating pattern produce visible light of a wavelength emission maxima in the range of from 400 nm to 700 nm under incident white light.

19. A nail varnishing system, comprising:
a nail varnish composition including a plurality of photonic particles, a block copolymer, or both a plurality of photonic particles and a block copolymer; wherein the photonic particles are configured to form photonic nanostructures including one or more photonic gyroid nanostructures; and
a stamp including a pattern of repeating nanostructures, wherein the stamp is configured to transfer the pattern of repeating nanostructures to a coating of the nail varnish composition to provide a pattern of repeating photonic nanostructures on the coating of the nail varnish composition.

20. A nail varnishing system, comprising:
a nail varnish composition including a plurality of photonic particles, a block copolymer, or both a plurality of photonic particles and a block copolymer; wherein the block copolymer self-organizes into lamellae, each lamella having a thickness of from 130 nm to 230 nm; and
a stamp including a pattern of repeating nanostructures, wherein the stamp is configured to transfer the pattern of repeating nanostructures to a coating of the nail varnish composition to provide a pattern of repeating photonic nanostructures on the coating of the nail varnish composition.

21. A nail vanishing kit, comprising:
precursors to a stamp;
a stamp mold including a pattern of repeating nanostructures; and
a nail varnish composition including a plurality of photonic particles, a block copolymer, or both a plurality of photonic particles and a block copolymer; wherein the block copolymer is selected from a poly(styrene-b-isoprene) diblock copolymer, poly(styrenesulfonate-methylbutylene), and polystyrene-poly(2-vinylpyridine).

22. The nail varnishing kit of claim 21, further comprising an ultraviolet light source.

23. The nail varnishing kit of claim 21, wherein the nail varnish composition is substantially dye-free.

24. The nail vanishing kit of claim 21, wherein the precursors include one or more of a vinyl end-capped oligomeric dimethyl siloxane, a methyl hydrosiloxane, a platinum catalyst, dimethylvinylated silica filler, and trimethylated silica filler.

25. The nail vanishing kit of claim 24, wherein the vinyl end-capped oligomeric dimethyl siloxane and methyl hydrosiloxane, when present, are provided in separate containers.

26. The nail varnishing kit of claim 24, wherein the vinyl end-capped oligomeric dimethyl siloxane and methyl hydrosiloxane are configured to copolymerize when contacted with one another.

27. The nail vanishing kit of claim 21, wherein the pattern of repeating nanostructures extends for a length of at least 0.4 mm and wherein each nanostructure has a dimension of from 100 nm to 1000 nm.

28. A method of forming a colored nail varnish coating on a nail surface, comprising:
applying a coating of a nail varnish composition onto a fingernail or toenail surface,
applying a stamp including a pattern of repeating nanostructures to the coating of nail varnish composition to transfer the pattern of repeating nanostructures to the coating of the nail varnish composition to provide a pattern of repeating photonic nanostructures on the coating of the nail varnish composition,
curing the coating of the nail varnish composition; and
removing the stamp from the cured coating of nail varnish composition to provide a nail varnish coating including a periodic light-diffractive repeating pattern configured to produce a structural color under incident white light;
wherein the nail varnish composition includes a plurality of photonic particles, a block copolymer, or both a plurality of photonic particles and a block copolymer; and wherein the block copolymer is selected from a poly(styrene-b-isoprene) diblock copolymer, poly(styrenesulfonate-methylbutylene), and polystyrene-poly (2-vinylpyridine).

29. The method of claim 28, wherein the nail varnish composition is substantially dye-free.

30. The method of claim 28, wherein curing the coating of the nail varnish composition includes exposing the coating of nail varnish composition to ultraviolet light.

31. The method of claim 28, wherein curing the coating of the nail varnish composition includes evaporating a solvent in the coating of nail varnish composition.

32. The method of claim 28, wherein the nail varnish coating including a periodic light-diffractive repeating pattern produces visible light of a wavelength emission maxima in the range of from 400 nm to 700 nm under incident white light.

33. The method of claim 28, wherein the fingernail or toenail surface includes an etched photonic pattern.

34. The method of claim 33, wherein the nail varnish coating including a periodic light-diffractive repeating pattern and the etched fingernail or toenail surface produce visible light of a wavelength emission maxima in the range of from 400 nm to 700 nm under incident white light.

35. A method of forming a nail varnish coating on a nail surface, comprising:

providing a first agent and a second agent to a stamp mold to form a stamp including a pattern of repeating nanostructures;

removing the stamp from the mold;

applying the stamp to a coating of an uncured nail varnish composition on a fingernail surface or a toenail surface to provide a nail varnish coating including repeating photonic nanostructures;

wherein the nail varnish composition includes a plurality of photonic particles, a block copolymer, or both a plurality of photonic particles and a block copolymer; and wherein the block copolymer is selected from a poly(styrene-b-isoprene) diblock copolymer, poly(styrenesulfonate-methylbutylene), and polystyrene-poly(2-vinylpyridine).

36. The method of claim 35, wherein the nail varnish composition is substantially dye-free.

37. The method of claim 35, further including curing the coating of the uncured nail varnish composition after applying the stamp to the coating of the uncured nail varnish composition.

38. The method of claim 35, wherein the nail varnish coating includes a periodic light-diffractive repeating pattern configured to produce a structural color under incident white light.

39. The method of claim 35, wherein curing the nail varnish composition includes exposing the nail varnish composition to ultraviolet light.

40. The method of claim 35, wherein curing the coating of the uncured nail varnish composition includes evaporating a solvent in the coating of uncured nail varnish composition.

41. The method of claim 35, wherein the nail varnish coating produces visible light of a wavelength emission maxima in the range of from 400 nm to 700 nm under incident white light.

42. The method of claim 35, wherein the fingernail surface or the toenail surface includes an etched pattern.

43. The method of claim 42, wherein the nail varnish coating and the etched pattern on the fingernail surface or toenail surface produces visible light of a wavelength emission maxima in the range of from 400 nm to 700 nm under incident white light.

* * * * *

UNITED STATES PATENT AND TRADEMARK OFFICE
CERTIFICATE OF CORRECTION

PATENT NO. : 10,362,850 B2
APPLICATION NO. : 15/403051
DATED : July 30, 2019
INVENTOR(S) : A. Guimont et al.

It is certified that error appears in the above-identified patent and that said Letters Patent is hereby corrected as shown below:

In the Claims

| Column | Line | Error |
|---|---|---|
| 12 (Claim 5, Line 18) | 56 | "vanish" should read --varnish-- |
| 13 (Claim 18, Line 2) | 37 | "produce" should read --produces-- |
| 13 (Claim 21, Line 2) | 66 | "vanishing" should read --varnishing-- |
| 14 (Claim 24, Line 1) | 14 | "vanishing" should read --varnishing-- |
| 14 (Claim 25, Line 1) | 19 | "vanishing" should read --varnishing-- |
| 14 (Claim 26, Line 1) | 23 | "vanishing" should read --varnishing-- |
| 14 (Claim 27, Line 1) | 27 | "vanishing" should read --varnishing-- |

Signed and Sealed this
Tenth Day of December, 2019

Andrei Iancu
*Director of the United States Patent and Trademark Office*